United States Patent [19]

Evans et al.

[11] Patent Number: 5,039,514
[45] Date of Patent: Aug. 13, 1991

[54] ALUMINA HYDRATE-CONTAINING TOOTHPASTE

[75] Inventors: Kenneth A. Evans; Kevin J. Wills; Anthony R. Emery, all of Buckinghamshire, England

[73] Assignee: Alcan International Limited, Montreal, Canada

[21] Appl. No.: 626,240

[22] Filed: Dec. 12, 1990

Related U.S. Application Data

[63] Continuation of Ser. No. 309,367, Feb. 13, 1989, abandoned.

[30] Foreign Application Priority Data

Feb. 12, 1988 [GB] United Kingdom ................. 8803328

[51] Int. Cl.$^5$ .......................... A61K 7/18; A61K 7/16
[52] U.S. Cl. ......................................... 424/52; 424/49
[58] Field of Search .................................... 424/49, 52

[56] References Cited

U.S. PATENT DOCUMENTS

| 2,010,910 | 8/1935 | Atkins | 424/49 |
|---|---|---|---|
| 2,550,207 | 4/1951 | Tainter et al. | 424/49 |
| 3,003,919 | 10/1961 | Broge | 424/49 |
| 3,662,060 | 5/1972 | Clippingdale et al. | 424/57 |
| 3,670,076 | 6/1972 | Muhler | 424/49 |
| 3,678,155 | 7/1972 | Clippingdale et al. | 424/52 |
| 3,822,345 | 7/1974 | Murray et al. | 424/52 |
| 3,957,968 | 5/1976 | Cordon . | |
| 4,034,076 | 7/1977 | Coulson et al. | 424/49 |
| 4,046,872 | 9/1977 | Mitchell et al. . | |
| 4,098,878 | 7/1978 | Baines et al. . | |
| 4,118,471 | 10/1978 | Pensak | 424/52 |
| 4,122,164 | 10/1978 | Mitchel et al. . | |
| 4,123,517 | 10/1978 | Baines et al. | 424/52 |
| 4,168,301 | 9/1979 | Pugh et al. | 424/52 |
| 4,212,856 | 7/1980 | Hoyles | 424/52 |
| 4,343,786 | 8/1982 | Baines et al. | 424/52 |
| 4,346,072 | 8/1982 | Baines et al. | 424/49 |
| 4,529,584 | 7/1985 | Mulvey et al. | 424/52 |
| 4,529,585 | 7/1985 | Hayes | 424/52 |
| 4,582,697 | 4/1986 | Cristol et al. . | |
| 4,781,982 | 11/1988 | Musselman et al. | 424/52 |

FOREIGN PATENT DOCUMENTS

| 633845 | 12/1949 | United Kingdom . |
|---|---|---|
| 1277585 | 10/1969 | United Kingdom . |
| 1188353 | 4/1970 | United Kingdom . |
| 1310374 | 3/1973 | United Kingdom . |
| 1373001 | 11/1974 | United Kingdom . |
| 1442395 | 7/1976 | United Kingdom . |
| 1475252 | 6/1977 | United Kingdom . |
| 1491211 | 11/1977 | United Kingdom . |
| 1537823 | 1/1979 | United Kingdom . |
| 2009596 | 6/1979 | United Kingdom . |
| 1560913 | 2/1980 | United Kingdom . |
| 1587608 | 4/1981 | United Kingdom . |
| 2061727 | 5/1981 | United Kingdom . |

OTHER PUBLICATIONS

Mordini and Cristol, "Production of Alumina Trihydrate for Non-Metallurgical Uses", Light Metals, pp. 325-336 (1983).

J. Scott, Effect of Seed and Temperature on the Particle Size of Bayer Hydrate. The British Aluminium Company, Ltd., N.Y.; Feb. 1962.

Sumitomo Brochure (English language version), pp. 2, 8 and 9. Jun. 1985.

Kirk-Othmer Encyclopedia of Chemical Technology 3rd ed., vol. 2 (1978); pp. 218-244 Aluminum Oxide (Alumina).

Mordini et al. C.A. 99:55753x (1983).

Evans et al. C.A. 112:83887z (1990) of EP 328406 Aug. 16, 1989.

Evans et al. C.A. 112:83888A (1990) of EP 328407 Aug. 16, 1989.

Primary Examiner—Shep K. Rose
Attorney, Agent, or Firm—Browdy and Neimark

[57] ABSTRACT

This invention relates to toothpaste containing an alumina hydrate abrasive and a source of fluoride.

According to the invention, there is provided a toothpaste containing a source of fluoride ions and unmilled, precipitated alumina trihydrate as an abrasive, wherein the alumina trihydrate particles have a median particle size of at least 3 micrometers.

The median particle size of the alumina trihydrate is preferably below 30 micrometers, more preferably from 5 to 20 micrometers, and most preferably 8 to 12 micrometers.

It has been found that the use of an unmilled alumina trihydrate, obtained by precipitation, substantially reduces the loss of available fluoride on storage whereas the use of a milled alumina trihydrate causes significant loss of available fluoride.

14 Claims, No Drawings

ALUMINA HYDRATE-CONTAINING TOOTHPASTE

This application is a continuation of application Ser. No. 07/309,367, filed Feb. 13, 1989 now abandoned.

This invention relates to toothpaste containing an alumina hydrate abrasive and a source of fluoride ions.

Toothpastes containing available fluoride, that is a source of fluoride ions which are available for protecting the user's teeth against caries, are in general use. A common constituent used as an available fluoride source is sodium monofluorophosphate. Other sources are sodium fluoride and stannous fluoride. Periodontal reagents to prevent plaque, and anti-bacteriological reagents may also be present. Toothpaste also contains a particulate abrasive such as alumina trihydrate, calcium carbonate, silica or dicalcium phosphate. The median particle size of the abrasive is generally not more than about 30 micrometers because particles having a larger size, e.g. 50 micrometers, tend to be perceived as "gritty" in texture which is undesirable in a toothpaste. As the particle size is reduced a "smoother" texture is obtained but the cleaning power of such particles becomes less. A good abrasive effect is generally not achieved with particles below about 3 micrometers. When alumina trihydrate is used as the abrasive, particles in this desired size range are generally produced by attrition milling of coarser material before it is incorporated into the toothpaste. Examples of such known toothpastes are given in GB-A-1277585, GB-A-1491211, GB-A-1537823, GB-A-1475252, GB-A-1587608, U.S. Pat. No. 4,122,164, GB-A-1188353, U.S. Pat. No. 3,957,968, GB-B-2009596, GB-A-1310374, GB-A-1373001, GB-A-1442395, U.S. Pat. Nos. 4,046,872, 4,098,878, GB-A-1560913, GB-B-2061727, and GB-A-633845.

Toothpaste is often stored in its container for a period of months, or even for years before use and it has been found that the content of available fluoride in the toothpaste tends to fall on storage, particularly at elevated temperatures. It is believed that this fall is due to reaction of the fluoride source with the abrasive, whereby some of the fluoride ions are rendered inactive. This fall on storage may render the available fluoride content of a given pack of toothpaste uncertain, and to achieve the minimum desired content of available fluoride the amount of fluoride source added to the toothpaste on manufacture has to be increased. This increases the cost of the product, and addition of fluoride source beyond a certain limit may be undesirable for other reasons.

It has now been found that the use of an unmilled alumina trihydrate, obtained by precipitation, substantially reduces the loss of available fluoride on storage, whereas the use of a milled alumina trihydrate causes significant loss of available fluoride. The reasons for this difference in behaviour are not fully understood but it is believed that fracture of the alumina trihydrate particles during milling produces an increased number of chemically and/or physically active sites on the particles' surfaces which appear to be responsible, at least in part, for the perceived reduction in the amount of available fluoride in toothpaste, particularly after storage.

According to the present invention there is provided a toothpaste containing a source of fluoride ions and unmilled, precipitated alumina trihydrate as an abrasive, wherein the alumina trihydrate particles have a median particle size of at least 3 micrometers.

The median particle size of the alumina trihydrate is preferably below 30 micrometers, more preferably from 5 to 20 micrometers, and most preferably from 8 to 12 micrometers.

The content of alumina trihydrate particles may be within the range normally used for abrasives in toothpaste, generally from 20 to 60% by weight. When the abrasive particles have a relatively narrow particle size distribution a relatively low abrasive content, e.g. 20 to 50% by weight, can be used to achieve the desired toothpaste viscosity.

The content of the source of fluoride ions may be within the range normally used in toothpaste, generally from 0.1 to 1% by weight.

When sodium monofluorophosphate is used as the source of available fluoride it may be present in an amount of about 0.8% of the weight of the toothpaste.

The toothpaste may contain other constituents which are conventionally used. A typical formulation is about 50% by weight of alumina trihydrate as abrasive, about 27% by weight of 70% w/w sorbitol syrup, about 1% by weight of sodium carboxymethyl cellulose, about 0.2% by weight of sodium saccharin, about 0.2% by weight of benzoic acid, about 1% by weight of flavour, about 1.5% by weight of a surfactant such as sodium lauryl sulphate and about 0.8% of sodium monofluorophosphate as a source of fluoride, with the remainder water. Peridontal reagents such as Hibitane (supplied by ICI plc) may also be present. The toothpaste may be made by a conventional method in which the constituents other than the surfactant and flavour are mixed in a high-speed disperser. The paste is then transferred to a slow speed mixer where the surfactant and flavour are added and the product is de-aerated. The toothpaste is then sealed in containers, such as tubes.

It has been found that an alumina trihydrate having a narrow particle size distribution can be added at a lower addition level than normal milled products to achieve a paste of the correct viscosity. This gives benefits of lower paste density and improved cost effectiveness. It is also known that total and soluble soda contents of alumina trihydrate affect the retained available fluoride in toothpaste. In general the lower the total and soluble soda the higher the retained available fluoride. Thus a reduction in the amount of aluminium trihydrate content is beneficial.

Preferably the particle size distribution for the alumina trihydrate particles, as defined by the ratio $(d_{10}-d_{90})/d_{50}$, is less than 1.3, and desirably less than 1.0, wherein $d_{10}$, $d_{50}$ and $d_{90}$ are the sizes for which 10%, 50% and 90%, respectively, of the particles are larger than that size.

Toothpastes according to the invention will be described by way of illustration in the following Examples. In the Examples the toothpaste formulations used are as set out in Table I.

TABLE 1

| Toothpaste Formulations | | | |
|---|---|---|---|
| | Formulation (% by weight) | | |
| | 1 | 2 | 3 |
| Alumina Trihydrate | 52.00 | 45.00 | 52.00 |
| Sorbitol (70% w/w) | 27.00 | 27.00 | 27.00 |
| Sodium Carboxymethyl Cellulose | 1.10 | 1.10 | 1.10 |
| Sodium Saccharin | 0.20 | 0.20 | 0.20 |
| Sodium Monofluorophosphate | 0.80 | 0.80 | — |
| Sodium Fluoride | — | — | 0.24 |
| Benzoic Acid | 0.15 | 0.15 | 0.15 |

TABLE 1-continued

Toothpaste Formulations

| | Formulation (% by weight) | | |
|---|---|---|---|
| | 1 | 2 | 3 |
| Sodium Lauryl Sulphate | 1.50 | 1.50 | 1.50 |
| Sodium Benzoate | 0.20 | 0.20 | 0.20 |
| Water | 17.05 | 24.05 | 17.61 |
| Total | 100.00 | 100.00 | 100.00 |

EXAMPLE 1

Samples of toothpaste were prepared by a standard method using a variety of milled and precipitated alumina trihydrate sources. The toothpaste samples were stored for 3 months at a constant temperature of 37° C. and the available fluoride content, expressed as the percentage of the original fluoride content, was then measured as follows:

A $10\pm0.1$ g sample of the paste was placed in a dry 150 ml beaker. Water, 40 g, was added and the mixture was stirred for 10 minutes so that no solid matter remained undispersed. The slurry was then centrifuged for 20 minutes with a force of 2,500 g. An aliquot, 5 ml, of the supernatant was transferred to a distillation flask fitted for steam distillation. Sulphuric acid (1:1), 50 mls, was added and the flask was heated. The temperature of the solution was regulated at 160° C.$\pm 20°$ C. Distillation was continued until 500 mls of distillate had been collected. A 25 ml aliquot of the distillate was transferred to a 50 ml graduated flask and was then diluted to volume with lanthanum alizarin blue. The solution was allowed to stand for 30 minutes and then the absorbance at 622 nm was measured. Total soluble fluoride was determined by reference to a calibration chart prepared using sodium fluoride standards.

The results obtained are presented in Table 2.

TABLE 2

| Trihydrate Sample | Formulation | Production Route | Mean Grain Size, Micrometers | % Retained Available Fluoride |
|---|---|---|---|---|
| A | 1 | Milled | 10 | 83 |
| B | 1 | Milled | 8 | 74 |
| C | 1 | Milled | 6 | 67 |
| D | 1 | Milled | 13 | 89 |
| E | 1 | Milled | 18 | 92 |
| F | 1 | Precipitated | 9.5 | 98 |
| G | 2 | Precipitated | 5.3 | 97 |

It will be seen that the fluoride retention performance of the precipitated alumina trihydrates is superior to that of the milled alumina trihydrates.

EXAMPLE 2

Samples of toothpaste were prepared by a standard method using a milled and a variety of precipitated alumina trihydrate sources. The toothpaste samples were stored for 9 weeks at a constant temperature of 49° C. and the available fluoride content, expressed as the percentage of the original fluoride content, was then measured as follows:

The total soluble fluoride content of the paste was determined by a technique described by Cropper and Puttnam (Journal of the Society of Cosmetic Chemistry, Vol. 21, (1970), pp. 533-540). The method is based on direct conversion in acid conditions, which also effects hydrolysis of monofluorophosphate, of the fluoride into its fluorosilane derivative. This derivative is extracted into benzene, containing pentane as an internal standard, and the resultant solution analysed by gas chromatography.

The results obtained are presented in Table 3.

TABLE 3

| Trihydrate Sample | Formulation | Production Route | Mean Grain Size, Micrometers | % Retained Available Fluoride |
|---|---|---|---|---|
| A | 1 | Milled | 10 | 73 |
| H | 2 | Precipitated | 3.5 | 94 |
| J | 2 | Precipitated | 5.5 | 85 |
| K | 2 | Precipitated | 9.0 | 95 |

It will be seen that the fluoride retention performance of the precipitated alumina trihydrates is superior to that of the milled alumina trihydrate. It will also be noted that storage at higher temperatures leads to higher loss of available fluoride. For trihydrate sample A the loss at 37° C. was 17% (Example 1), but at 49° C. was 27% (Example 2), although it will be noted that the analysis methods used in the two Examples were not the same.

EXAMPLE 3

Samples of toothpaste were prepared by a standard method using milled and precipitated alumina trihydrate sources. The toothpaste samples were stored for 9 weeks at a constant temperature of 49° C. and the available fluoride contents, expressed as the percentage of the original fluoride content, were measured as in Example 2.

The results obtained are presented in Table 4.

TABLE 4

| Trihydrate Sample | Formulation | Production Route | Mean Grain Size in Micrometers | % Retained Available Fluoride |
|---|---|---|---|---|
| A | 3 | Milled | 10 | 67 |
| F | 3 | Precipitated | 9.5 | 83 |

It will be seen that the fluoride retention performance of the precipitated alumina trihydrate is superior to that of the milled alumina trihydrate.

EXAMPLE 4

Samples of toothpaste were prepared by a standard method from precipitated alumina trihydrates having the particle size distributions referred to in Table 5.

TABLE 5

| Trihydrate Sample | Formulation | Particle Size Distribution (Micrometers) | | | $d_{10} - d_{90}$ / $d_{50}$ |
|---|---|---|---|---|---|
| | | $d_{10}$ | $d_{50}$ | $d_{90}$ | |
| F | 1 | 21.0 | 9.5 | 3.5 | 1.84 |
| L | 2 | 15.4 | 10.4 | 5.5 | 0.95 |

To achieve the same toothpaste viscosity, it was found that the loadings of alumina trihydrate were 52% for sample F and 45% for sample L. As can be seen from the results of Table 5 the alumina trihydrate having the narrower particle-size distribution as defined by the ratio $(d_{10}-d_{90})/d_{50}$ gave the benefit of a lower alumina trihydrate loading and consequently a lower toothpaste density.

Milled alumina trihydrates of 5 to 30 micrometers are normally manufactured from coarse precipitated material of about 60 micrometers using a fluid energy mill, see British Patent No. 1,537,823. Commercially available milled alumina trihydrates include those sold by BA Chemicals Ltd. under the trade mark BACO AF.

Various methods can be used to prepare precipitated alumina trihydrates. For example, J. Scott ('Effect of Seed and Temperature on the Particle Size of Bayer Hydrate', paper presented at the International Symposium on the Extractive Metallurgy of Aluminium, New York, February 1962) reported that a 10.5 micrometers precipitated alumina trihydrate can be produced by the following method:

a. alumina trihydrate seed (4.1 micrometers) is obtained by wet sieving and elutriation of coarse Bayer alumina trihydrate.
b. The seed at a concentration of 40 g per liter is added to sodium aluminate liquor (130 g/l $Na_2O$, 130 g/l $Al_2O_3$).
c. The solution is then decomposed at 50° C.

A precipitated alumina trihydrate having a median particle size of 9 micrometers is also available commercially from Nippon Light Metal Company of Japan.

Although heretofore the disclosed precipitated alumina trihydrate has been described as the sole abrasive in the toothpaste composition, it can be supplemented by one or more other abrasives such as calcium carbonate. Furthermore the disclosed precipitated alumina trihydrate can be blended with milled alumina trihydrate if desired. Because of the viscosity considerations referred to previously it is desirable that any other abrasive material which is used to supplement the precipitated alumina trihydrate has a particle size and a particle size distribution within the ranges preferred for the precipitated alumina trihydrate.

We claim:

1. In a toothpaste containing (i) a source of an effective amount of fluoride ions and (ii) an abrasion effective amount of alumina trihydrate as an abrasive having a particle size sufficiently great to have good abrasive effect but not so great as to provide a gritty texture, the improvement wherein
said alumina trihydrate consists essentially of unmilled, precipitated alumina trihydrate so as to provide said toothpaste with less reduction of available fluoride after storage, as compared to fluoride containing toothpaste having milled alumina trihydrate particles of the same percentage by weight and of the same median particle size.

2. In a toothpaste containing (1) a source of an effective amount of fluoride ions and (ii) and an abrasive including an abrasion effective amount of alumina trihydrate having a particle size sufficiently great to have good abrasive effect but not so great as to provide a gritty texture, the improvement wherein
said abrasive consists of at least a first portion in the amount of at least 20% by weight based on the toothpaste of unmilled, precipitated alumina trihydrate so as to provide said toothpaste with less reduction of available fluoride after storage as compared to fluoride containing toothpaste having milled alumina trihydrate particles of the same percentage by weight and of the same median particle size, said median particle size of said first portion being about 3–30 micrometers and having a particle size distribution as defined by the ratio $(d_{10}-d_{90})/d_{50}$ of less than 1.3, said toothpaste being generally free of milled alumina trihydrate.

3. In a toothpaste consisting essentially of (1) a source of an effective amount of fluoride ions and (ii) an abrasive including an abrasion effective amount of alumina trihydrate having a particle size sufficiently great to have good abrasive effect but not so great as to provide a gritty texture, the improvement wherein
a major portion of said abrasive in the range of 20–60% by weight of said toothpaste consists of unmilled, precipitated alumina trihydrate so as to provide said toothpaste with less reduction of available fluoride after storage as compared to fluoride containing toothpaste having milled alumina trihydrate particles of the same percentage by weight and of the same median particle size, said unmilled alumina trihydrate having a median particle size being about 3–30 micrometers and having a particle size distribution as defined by the ratio $(d_{10}-d_{90})/d_{50}$ of less than 1.3, said toothpaste being generally free of milled alumina trihydrate.

4. A toothpaste according to claim 1 wherein the median particle size of the alumina trihydrate is below 30 micrometers, the abrasion-effective amount of alumina trihydrate is 20–60% by weight, and the therapeutically-effective amount of said source of fluoride ions is less than about 1.0%.

5. A toothpaste according to claim 1 wherein the median particle size of the alumina trihydrate is about 3–30 micrometers, the content of alumina trihydrate particles is in the range of 20–50% by weight, and the particle size distribution for the alumina trihydrate particles as defined by the ratio $(d_{10}-d_{90})/d_{50}$ is less than 1.3.

6. A toothpaste according to claim 1 in which the median particle size of the alumina trihydrate is below 30 micrometers.

7. A toothpaste according to claim 1 having a content of alumina trihydrate particles of from 20 to 60% by weight.

8. A toothpaste according to claim 1 in which the source of fluoride ions is present in an amount of from 0.1 to 1% by weight.

9. A toothpaste containing (i) a therapeutically-effective amount in the range of 0.1–1% by weight of a source of fluoride ions and (ii) an alumina trihydrate abrasive consisting essentially of an abrasion-effective amount in the range of 20–60% by weight of unmilled, precipitated alumina trihydrate, wherein the alumina trihydrate particles have a median particle size of 3–30 micrometers but not so great as to provide a gritty texture, said toothpaste being essentially free of milled alumina trihydrate, said toothpaste having less reduction of available fluoride, after storage, than toothpaste having milled alumina trihydrate particles of the same percentage by weight content and the same median particle size.

10. A toothpaste according to claim 6, in which the median particle size of the alumina trihydrate is from 5 to 20 micrometers.

11. A toothpaste according to claim 10, in which the median particle size of the alumina trihydrate is from 8 to 12 micrometers.

12. A toothpaste according to claim 7 having a content of alumina trihydrate particles of from 20 to 50% by weight and a particle size distribution for the alumina trihydrate particles as defined by the ratio $(d_{10}-d_{90})/d_{50}$ of less than 1.3.

13. A toothpaste according to claim 12 wherein the particle size distribution for the alumina trihydrate particles as defined by the ratio $(d_{10}-d_{90})/d_{50}$ is less than 1.0.

14. A toothpaste according to claim 13 wherein said source of fluoride ions is present in an amount of 0.1 to 1% by weight.

* * * * *